(12) United States Patent
Gifford et al.

(10) Patent No.: US 10,253,350 B2
(45) Date of Patent: Apr. 9, 2019

(54) SEPARATION OF MOLECULES USING NANOPILLAR ARRAYS

(71) Applicant: INTERNATIONAL BUSINESS MACHINES CORPORATION, Armonk, NY (US)

(72) Inventors: Stacey M. Gifford, Ridgefield, CT (US); Joshua T. Smith, Hudson, NY (US); Benjamin H. Wunsch, Mt. Kisco, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 75 days.

(21) Appl. No.: 15/270,306

(22) Filed: Sep. 20, 2016

(65) Prior Publication Data

US 2018/0080060 A1 Mar. 22, 2018

(51) Int. Cl.
*B01L 3/00* (2006.01)
*C12Q 1/6806* (2018.01)
*G01N 15/02* (2006.01)
*G01N 15/14* (2006.01)
*G01N 15/10* (2006.01)

(52) U.S. Cl.
CPC ...... *C12Q 1/6806* (2013.01); *B01L 3/502746* (2013.01); *B01L 3/502761* (2013.01); *G01N 15/02* (2013.01); *G01N 15/1056* (2013.01); *G01N 15/1459* (2013.01); *G01N 15/1463* (2013.01); *B01L 2200/0652* (2013.01); *B01L 2200/143* (2013.01); *B01L 2300/0816* (2013.01); *B01L 2300/0896* (2013.01); *B01L 2400/086* (2013.01); *G01N 2015/0288* (2013.01); *G01N 2015/1006* (2013.01); *G01N 2015/1081* (2013.01); *G01N 2015/1087* (2013.01); *G01N 2015/149* (2013.01)

(58) Field of Classification Search
CPC .................................................... C12Q 1/68
See application file for complete search history.

(56) References Cited

U.S. PATENT DOCUMENTS

| 2007/0026381 A1* | 2/2007 | Huang | B01L 3/502746 435/4 |
| 2007/0059781 A1* | 3/2007 | Kapur | B01L 3/502746 435/7.21 |
| 2013/0079251 A1* | 3/2013 | Boles | C12M 45/09 506/26 |

(Continued)

OTHER PUBLICATIONS

Chen et al., Concentrating genomic length DNA in a microfabricated array, Phys Rev Lett. May 15, 2015;114(19):198303. Epub May 15, 2015.*

Zeming et al., Real-time modulated nanoparticle separation with an ultra-large dynamic range, Lab Chip, 2016,16, 75-85, Nov. 17, 2015.*

(Continued)

*Primary Examiner* — Aaron A Priest
(74) *Attorney, Agent, or Firm* — Cantor Colburn LLP; Vazken Alexanian

(57) ABSTRACT

A technique relates to separation of a mixture. A nano-deterministic lateral displacement (nanoDLD) array is configured to separate the mixture in a fluid. A feedback system is configured to control a velocity of the fluid through the nanoDLD array. The feedback system is configured to control the velocity of the fluid to separate one or more entities in the mixture.

18 Claims, 18 Drawing Sheets

(56) References Cited

U.S. PATENT DOCUMENTS

| | | | |
|---|---|---|---|
| 2016/0047735 A1* | 2/2016 | Grisham | G01N 15/1484 |
| | | | 435/7.1 |
| 2016/0144361 A1 | 5/2016 | Astier et al. | |
| 2016/0144405 A1 | 5/2016 | Astier et al. | |
| 2016/0144406 A1 | 5/2016 | Astier et al. | |
| 2016/0146717 A1 | 5/2016 | Astier et al. | |
| 2016/0146718 A1 | 5/2016 | Astier et al. | |
| 2016/0146778 A1 | 5/2016 | Astier et al. | |
| 2017/0122937 A1* | 5/2017 | Arai | G01N 33/54313 |
| 2017/0209864 A1* | 7/2017 | Grisham | B01L 3/502746 |
| 2017/0268037 A1 | 9/2017 | Ionescu-Zanetti et al. | |
| 2017/0354362 A1 | 12/2017 | Xu et al. | |

OTHER PUBLICATIONS

McGrath et al., Deterministic lateral displacement for particle separation: a review, Lab Chip, 2014,14, 4139-4158, Sep. 4, 2014.*

Chen et al., "Concentrating Genomic Length DNA in a Microfabricated Array", Physical Review Letters, PRL 114, 198303, DOI: 10.1103/PhysRevLett.114.198303, 2015, pp. 1-5.

Huang et al., "Continuous Particle Separation Through Deterministic Lateral Displacement", Science 304, 987, DOI: 10.1126/science.1094567, 2004, pp. 1-5.

Kaji et al., "Separation of Long DNA Molecules by Quartz Nanopillar Chips under a Direct Current Electric Field", Anal. Chem. 76, 2004, pp. 15-22.

Yasui et al., "Arrangement of a Nanostructure Array to Control Equilibrium and Nonequilibrium Transports of Macromolecules", American Chemical Society, DOI: 10.1021/acs.nanolett.5b00783, Nano Lett. 2015, 15, pp. 3445-3451.

* cited by examiner

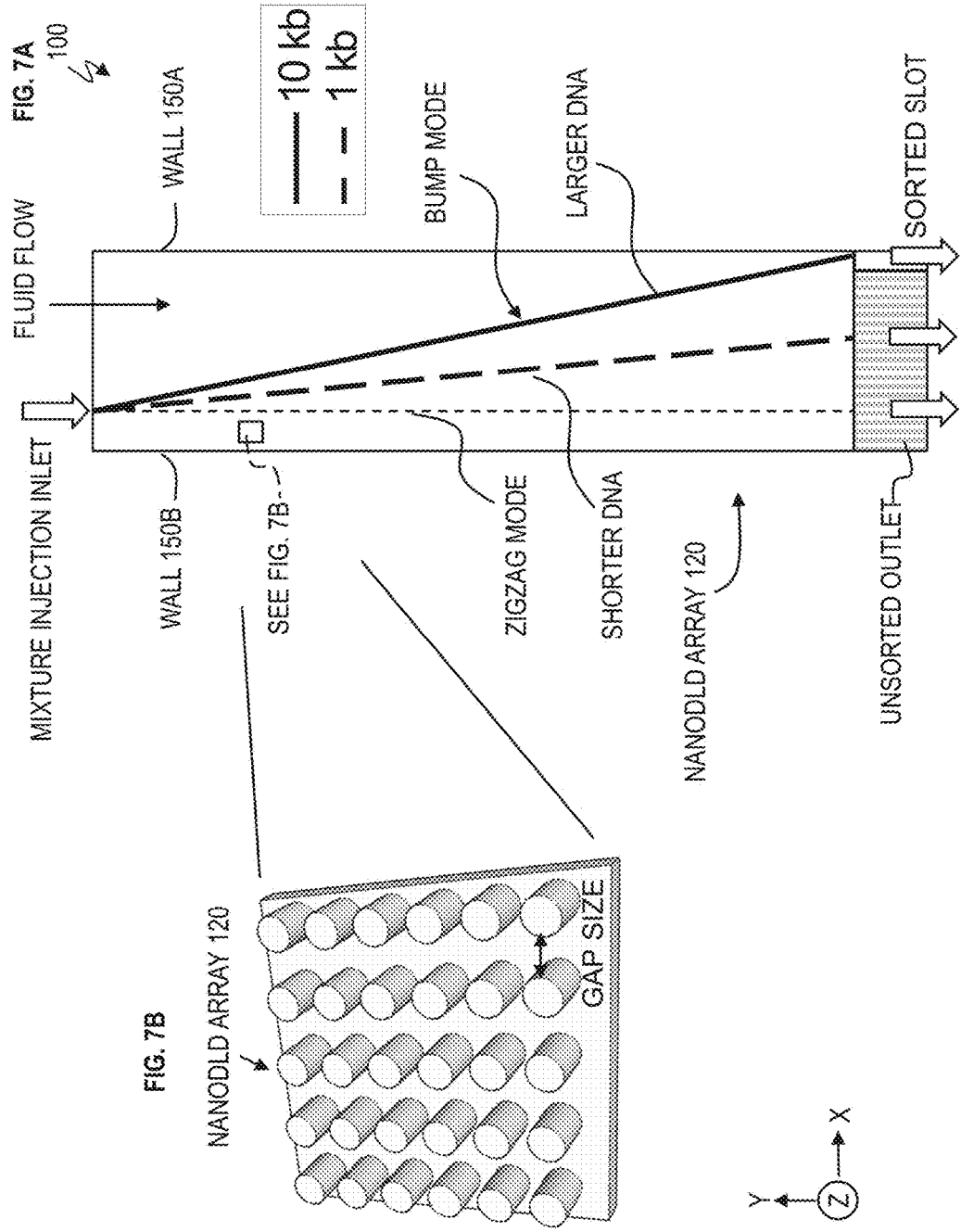

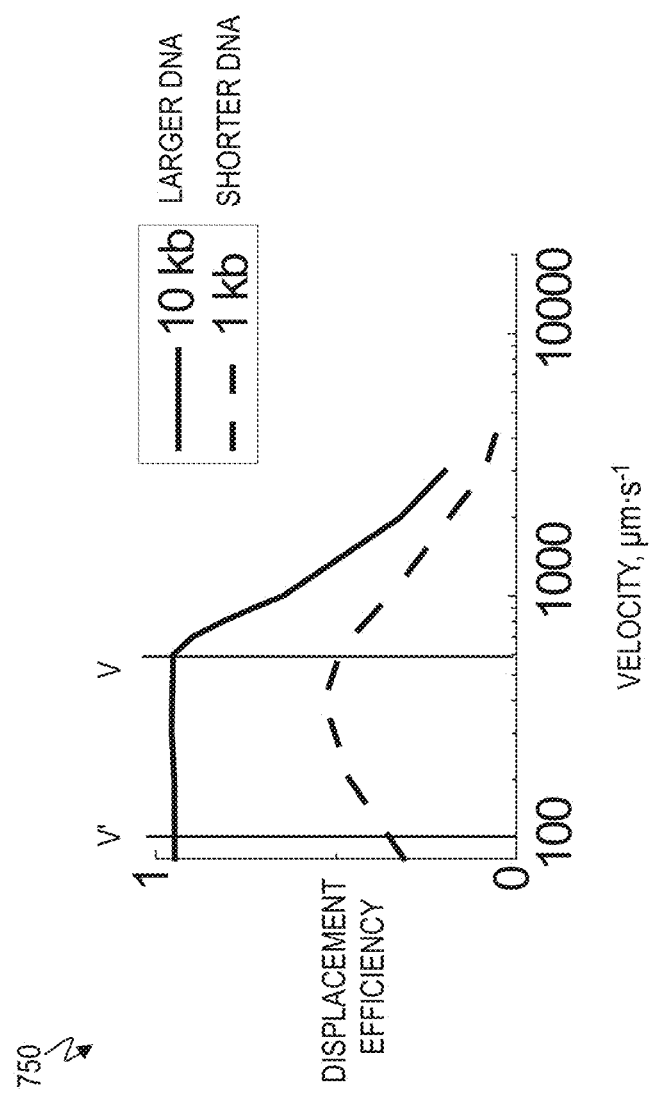

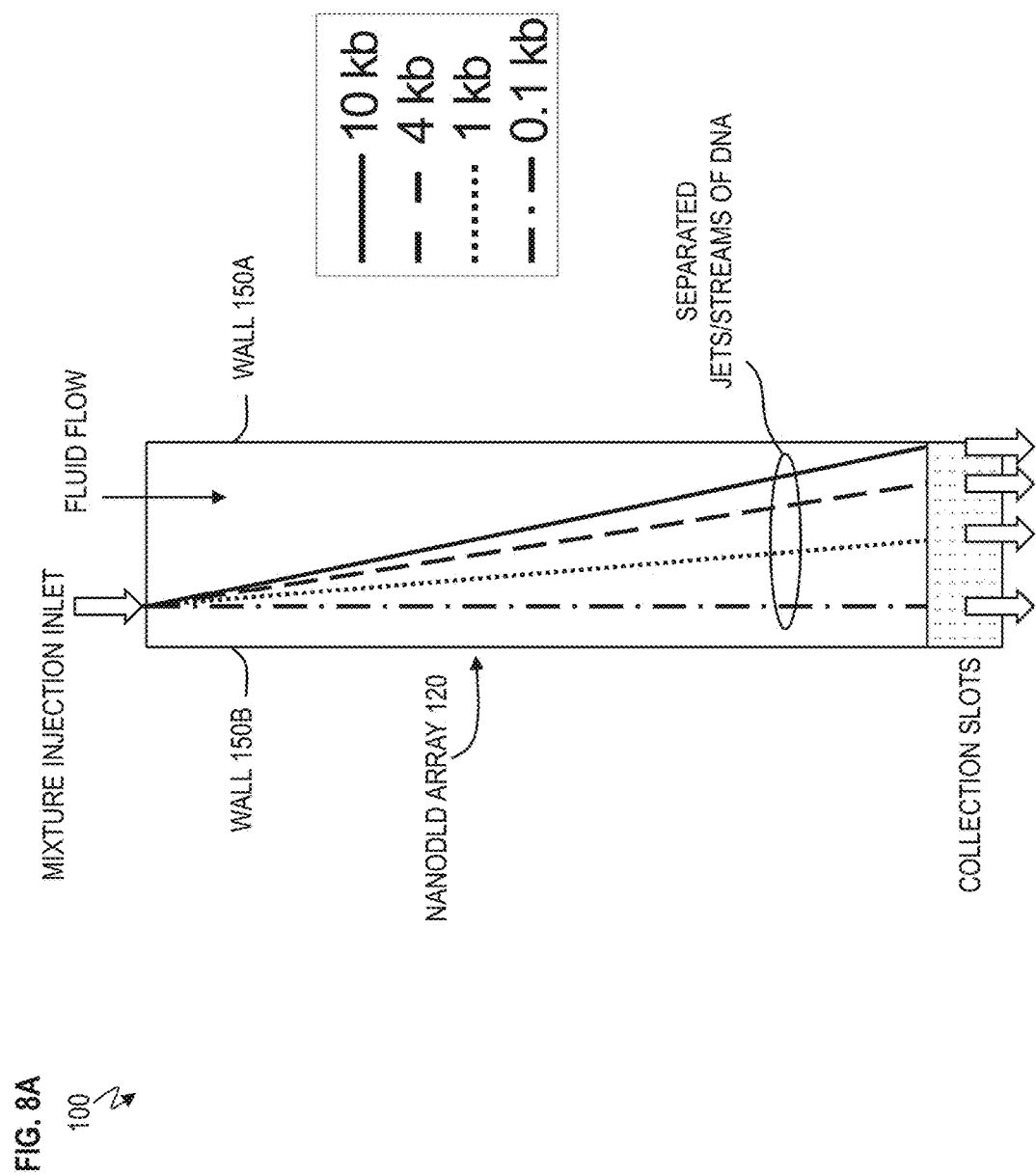

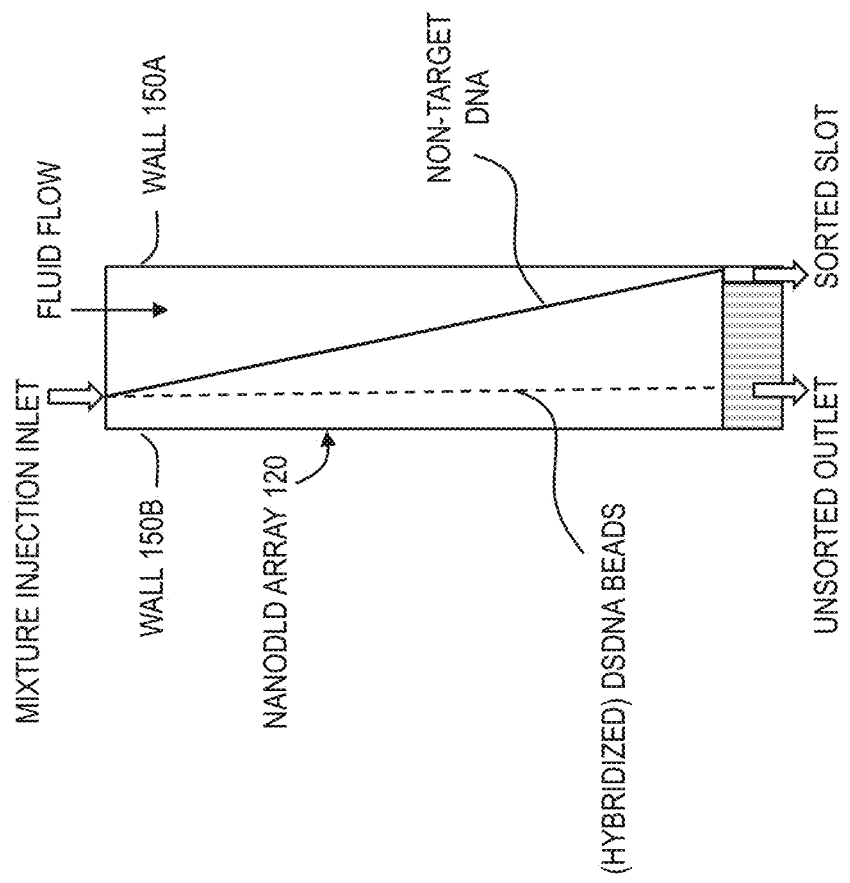

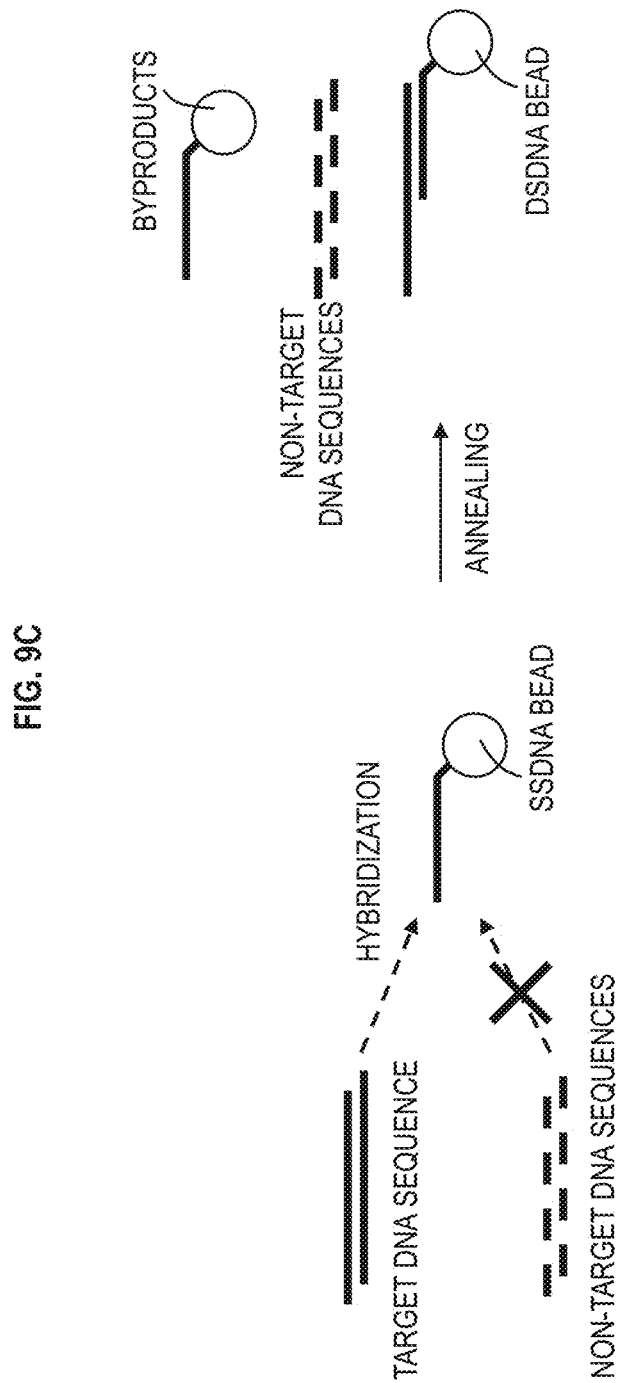

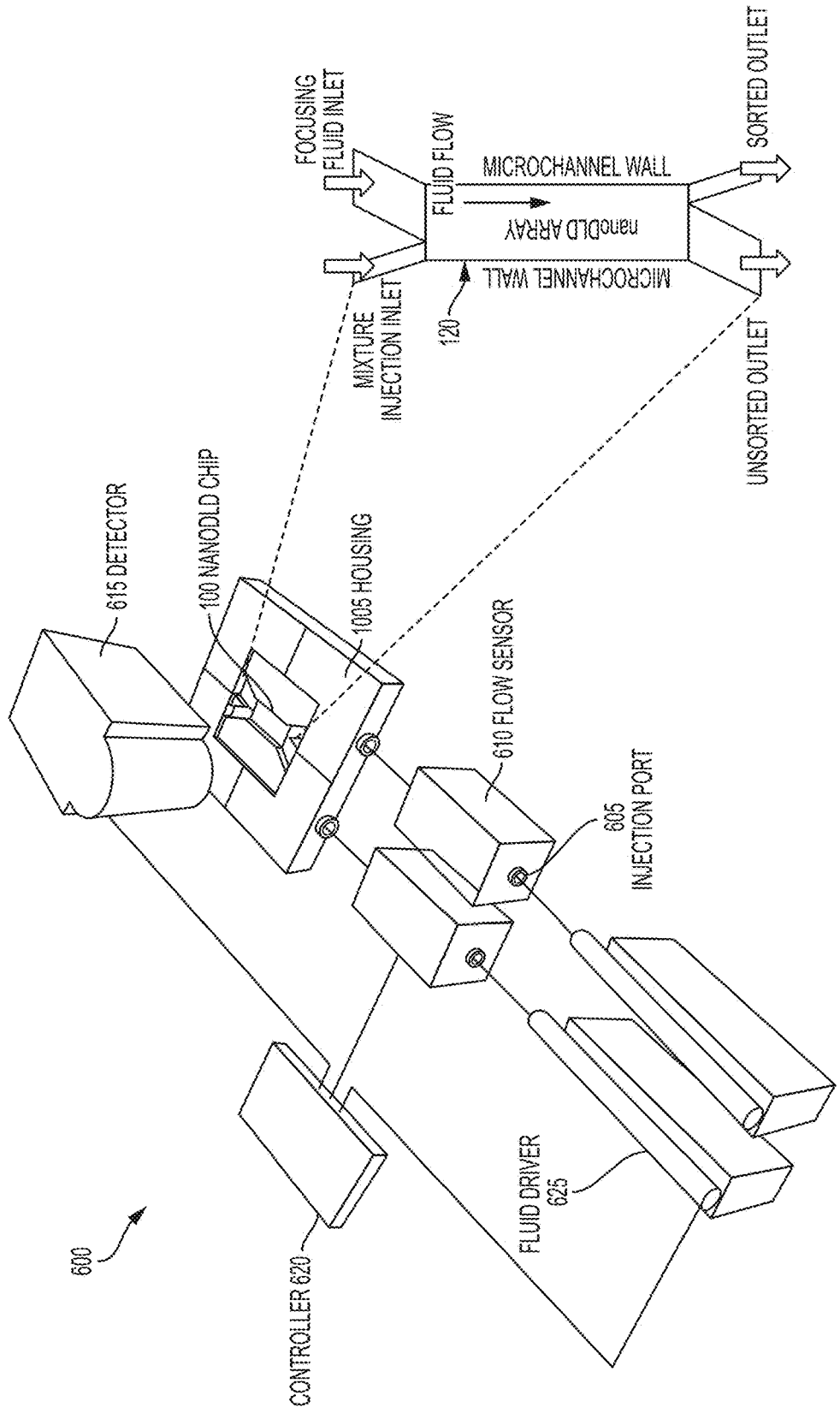

LOAD THE REQUISITE BUFFER SOLUTION INTO THE FLUID DRIVER AND INJECT THE BUFFER SOLUTION INTO THE NANODLD ARRAY, COMPLETELY WETTING THE FLOW SENSOR AND NANODLD DEVICE 1105

↓

LOAD A COMPLEX MIXTURE OF DIFFERENT DNA AND RNA STRANDS, REAGENTS, ENZYMES, MACROMOLECULES, MOLECULES, SURFACTANTS, SALTS, CATALYSTS, ETC., INTO THE NANODLD ARRAY THROUGH AN INJECTION PORT IN THE HOUSING, SUCH THAT COMPLEX MIXTURE IS FED INTO THE ARRAY IN A NARROW JET ON THE WALL OPPOSITE OF THE SORTED SLOT. 1110

↓

CONTROLLER IS PROGRAMMED WITH A LATERAL POSITION SET-POINT FOR THE DNA, WHICH IS TO BE MAINTAINED BY CONTROL OF THE VELOCITY IN WHICH THE LATERAL POSITION OF THE DNA DETERMINES THE DEGREE TO WHICH THE DNA IS SEPARATED FROM THE COMPLEX MIXTURE. 1115

↓

CONTROLLER ACTIVATES THE FLUID DRIVER, INITIATING AND RAMPING THE FLUID VELOCITY, WHICH IS MEASURED BY THE FLOW SENSOR 1120

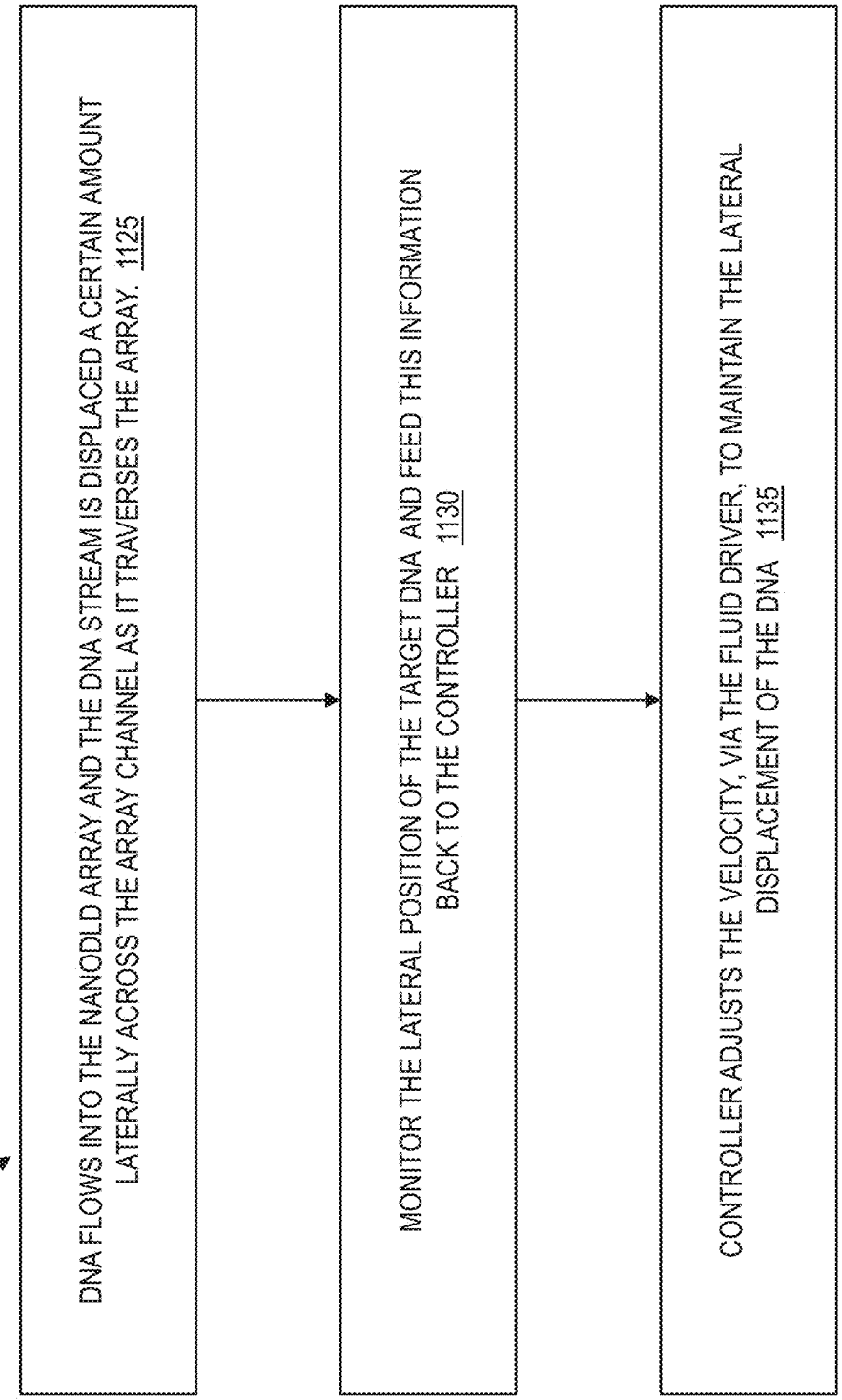

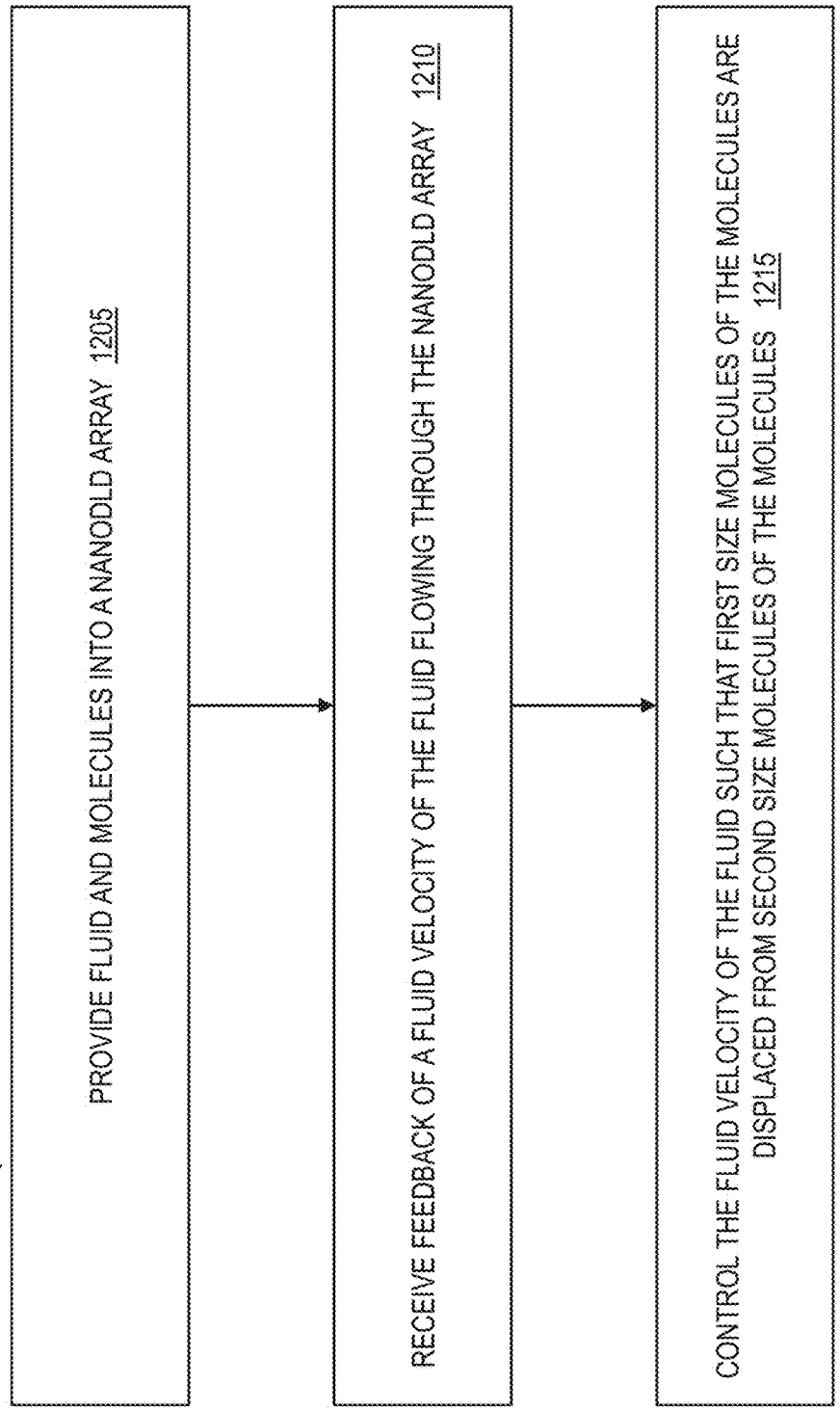

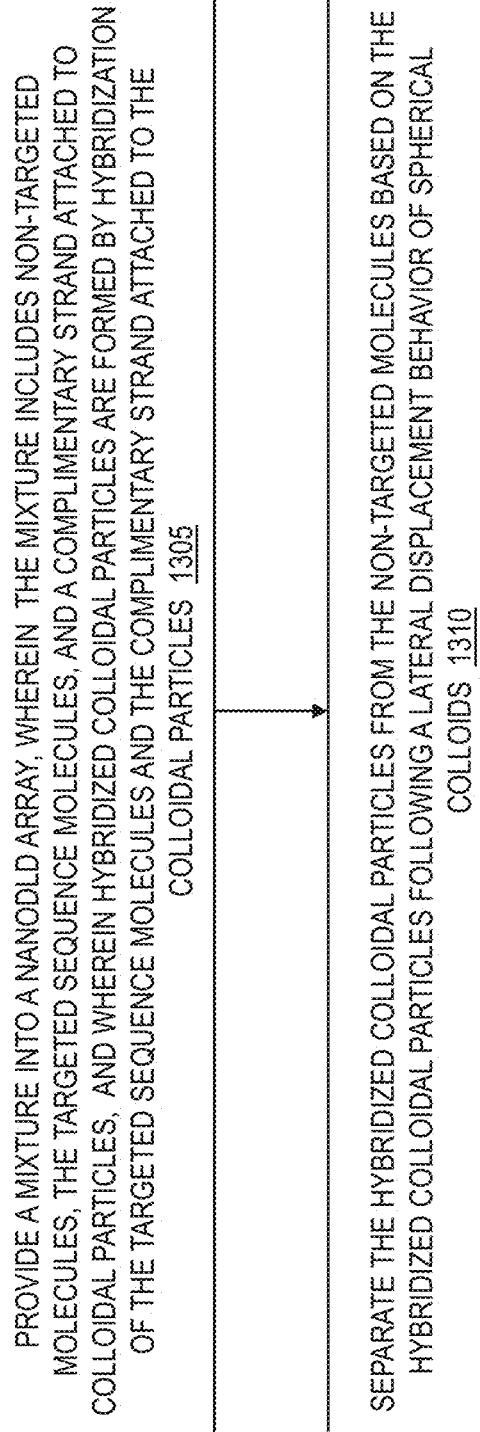

SEPARATION OF MOLECULES USING NANOPILLAR ARRAYS

BACKGROUND

The present invention relates to separation of molecules (such as DNA, RNA, etc.), and more particularly to separation of molecules via nano-deterministic lateral displacement using a pillar array.

The separation and sorting of biological entities, such as cells, proteins, deoxyribonucleic acid (DNA), ribonucleic acid (RNA), etc., is used in a vast number of biomedical applications including diagnostics, therapeutics, cell biology, and proteomics. Protein and DNA/RNA separation for analytical purposes is traditionally done by gel electrophoresis, where a protein mix is subjected to a strong electric field (typically 30 volts per centimeter (V/cm)). Proteins or DNA/RNA move through the gel at a rate depending on their size and surface charge.

SUMMARY

According to one or more embodiments, a system for separation of a mixture is provided. The system includes a nano-deterministic lateral displacement (nanoDLD) array configured to separate the mixture in a fluid, and a feedback system configured to control a velocity of the fluid through the nanoDLD array. The feedback system is configured to control the velocity of the fluid to separate one or more entities in the mixture.

According to one or more embodiments, a method of separating molecules is provided. The method includes providing fluid and molecules into a nanoDLD array, receiving feedback of a fluid velocity of the fluid flowing through the nanoDLD array; and controlling the fluid velocity of the fluid such that first size molecules of the molecules are displaced from second size molecules of the molecules.

According to one or more embodiments, a method of separating targeted sequence molecules is provided. The method includes providing a mixture into a nanoDLD array, where the mixture includes non-targeted molecules, the targeted sequence molecules, and a complimentary strand attached to colloidal particles. Hybridized colloidal particles are formed by hybridization of the targeted sequence molecules and the complimentary strand attached to the colloidal particles. Also, the method includes separating the hybridized colloidal particles from the non-targeted molecules based on the hybridized colloidal particles following a lateral displacement behavior of spherical colloids.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

FIG. 7A is a schematic illustrating that the nanoDLD array is utilized for deterministic lateral displacement according to one or more embodiments.

FIG. 7B is an enlarged view highlighting the nanoDLD array 120 in FIG. 7A according to one or more embodiments.

FIG. 7C is a graph depicting the relationship between the displacement efficiency and velocity plotted for a given gap size and DNA length in FIG. 7A according to one or more embodiments.

FIG. 8A is a schematic illustrating the nanoDLD array utilized for deterministic lateral displacement according to one or more embodiments.

FIG. 9A is a schematic of hybridized bead dsDNA separation according to one or more embodiments.

FIG. 9C depicts an example of hybridizing a single strand DNA bead with its complementary target DNA sequence according to one or more embodiments.

FIG. 10A depicts a machine layout of the machine according to one or more embodiments.

FIG. 10B is an enlarged view of the nanoDLD array chip in the machine of FIG. 10A according to one or more embodiments.

FIGS. 11A and 11B together illustrate a flow chart depicting an example operation the sorting machine according to one or more embodiments.

FIG. 12 is a flow chart of a method of separating molecules according to one or more embodiments.

FIG. 13 is a flow chart of method of separating targeted sequence molecules from a mixture according to one or more embodiments.

DETAILED DESCRIPTION

Figure 1:
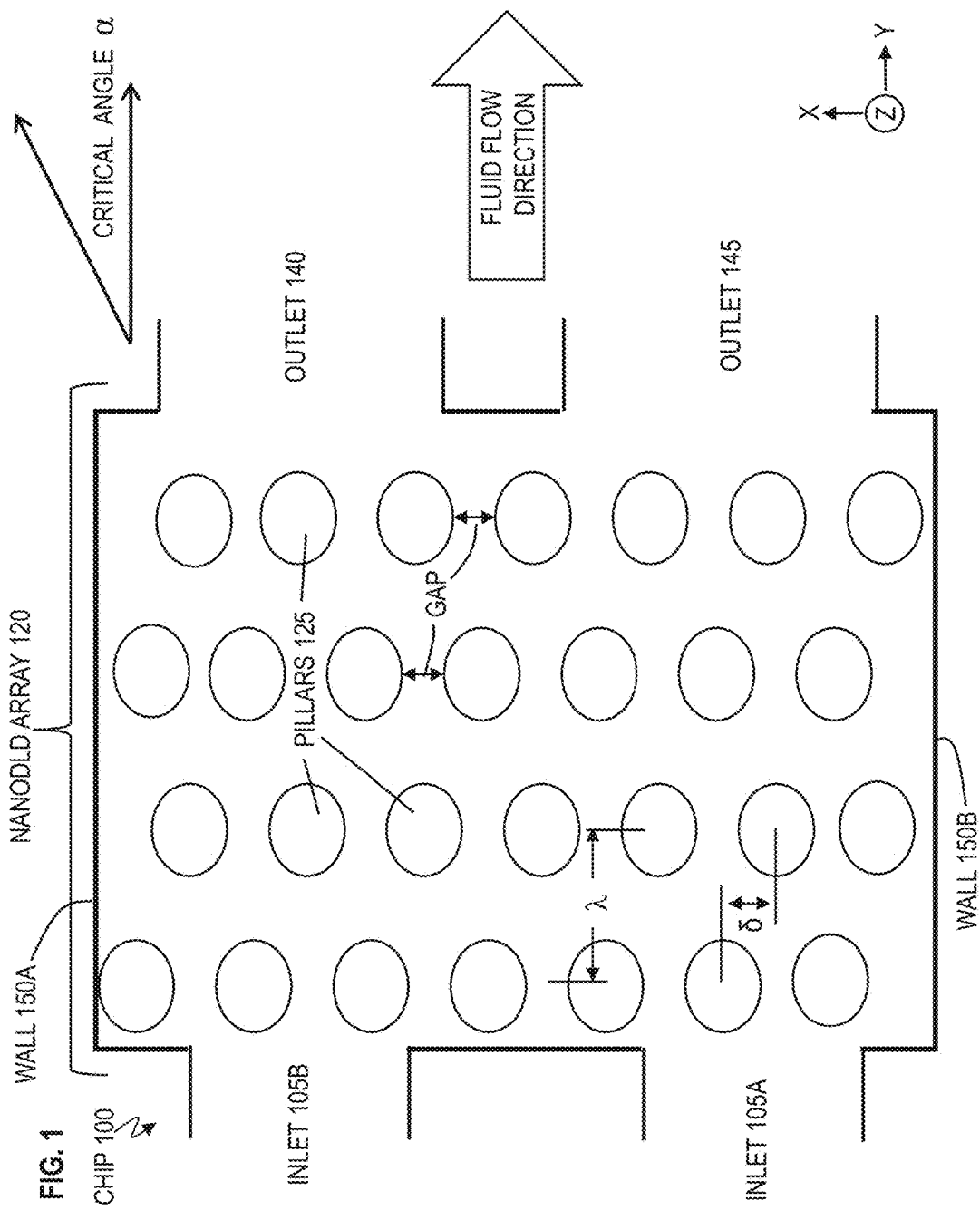
FIG. 1 is a top view illustrating a chip (fluidic device) having a pillar array according to one or more embodiments.

The preparation, purification and identification of DNA are relevant to several fields of biology and biotechnology including genomic sequencing, gene therapy, synthetic biology, and genetic engineering. The range of technical challenges involved in purification diverges with the population size of DNA that is to be isolated. For large populations of DNA molecules, obtained from an amplification process such as PCR, the amplified sequence needs to be purified from the requisite enzymes, primers, substrates, reagents and byproducts associated with amplification process. For current state-of-the-art sequencing, read frames of hundreds to thousands of basepairs are used. On the opposite side of the spectrum, for small or dilute populations of rare DNA molecules, the challenge is to identify and capture with high fidelity these specific targets from a larger, and potentially very similar, pool of molecules. Gel electrophoresis is the current workhorse of DNA purification, and while it can provide high fidelity to single basepair resolution, it is limited by slow processing times (e.g., multiple hours) and batch processing. In addition, significant quantities of DNA are necessary for detection and extraction from gels, reducing the ability to isolate rare or low frequency sequences.

Deterministic lateral displacement (DLD) has emerged as a potential lab-on-a-chip technology for separation of microscopic particles and colloids by size using a physical, non-destructive method in continuous flow and with single particle resolution. Scientists at IBM® have recently extended this technology to the nanoscale level by providing novel nano-deterministic lateral displacement (nanoDLD) methodologies as described in U.S. Publication No. 2016/0144405, application Ser. No. 14/697,072, filed Apr. 27, 2015, which is herein incorporated by reference in its entirety. The novel nanoDLD methodologies allow separation of colloids down to 20 nanometers (nm) in diameter.

However, previous work has focused on either rigid spherical particles or elastic corpuscles such as blood cells, exosomes or parasites. The ability to separate DNA has been limited. For example, one state-of-the-art system has demonstrated on-chip separation of large DNA macromolecules (166 kilobases or kilo-basepairs (kbp)) in a microscopic DLD array; however, this method requires using a surfactant to condense the DNA in a tight coil, requiring further purification to remove the surfactant later, as well as an inability to separate strands <1,000 basepair.

Another state-of-the-art system has demonstrated that DNA can be separated in a microfluidic array with gap sizes from about 300 nm to about 1000 nm; however, the geometry of these arrays is not set for nanoDLD, using instead either a lattice aligned with the microchannel, or tilted at 45° degrees to the microchannel, which are not DLD control modes. More importantly, although state-of-the-art systems use pillars to effect separation, the separation is along the length of the microchannel (as would be seen in chromatography or gel electrophoresis) limiting it to batch or pulse mode operation. In contrast, nanoDLD separation is along the width of the microchannel, allowing continuous operation.

Currently there is no high resolution method for continuous separation of DNA on-chip in a nanofluidic system, especially with nanoDLD, and it is this capability that the embodiments described herein address.

According to one or more embodiments, a system provides a microfluidic chip that incorporates a nanoDLD pillar array built into a microchannel, as well as control hardware for monitoring and adjusting the speed of fluid flow within the fluidic chip. The nanoDLD spatially displaces, e.g., DNA across the width of the microchannel, with the dimensions of the pillar array determining the degree to which a given DNA strand length is displaced. The degree of displacement of a DNA strand within a nanoDLD array is anti-correlated with increasing speed. Thus, adjusting the flow velocity affects the degree of spatial displacement (e.g., lateral displacement). This allows a range of operation modes for selecting out and purifying different strand lengths from a complex mixture. As the system can be run continuously, purified DNA extracts can be accumulated and removed from the microfluidic chip for further analysis or application. The system is structured to take advantage of the behavior of DNA in a nanoDLD array to produce a separation technology that enables on-chip purification of genetic material from cellular extracts or transcription operations. The system can be integrated into schemes for searching for new genes or DNA constructs from a complex mixture.

FIG. 1 illustrates a chip 100 (fluidic device) having a nano-deterministic lateral displacement (nanoDLD) array 120 according to one or more embodiments. The nanoDLD array 120 includes an array of pillars 125 and can also be referred to as a pillar array or nanopillar array. The chip 100 has at least one inlet 105A to receive fluid containing a mixture of the different sized particles (i.e., biological entities) to be sorted. The inlet 105A can be an opening or hole in the walls around the nanopillar array 120 or can span the width of the nanopillar array 120 through which fluid (e.g., water, electrolyte solutions, organic solvents, etc.) and the mixture of particles (e.g., biological entities which can include DNA, RNA, etc.) can flow. In one implementation, there can be two or more inlets 105A and 105B. In this case, the inlet 105A receives input of the mixture to be sorted, and the mixture can be in a fluid (such as an electrolyte solution). The inlet 105B can be utilized to input a fluid not containing the mixture of the particles.

Particles having a size greater than the critical dimension are bumped (i.e., bump mode) through the nanoDLD array 120 in the direction of the critical angle α, and these particles larger than the critical dimension are laterally displaced in the x-axis and collected at outlet 140. The critical dimension is the size (e.g., diameter or length) of a round shaped particle and/or persistence length of a chain structure, such as DNA/RNA, that is too large to zigzag through the nanoDLD pillar array 120.

On the other hand, particles having a size smaller than the critical dimension zigzag (i.e., zigzag mode) through the nanoDLD array 120 in the direction of fluid flow, and these smaller particles are collected (with very little lateral displacement and/or relatively no lateral displacement in the x-axis) at the outlet 145. The particles having the size smaller than the critical dimension follow the direction of the fluid flow, and are sorted through the outlet 145. The outlets 140 and 145 can be openings through which the sorted particles can flow and be collected in bins after sorting. It is appreciated that although only two outlets 140 and 145 are depicted, there can more than two outlets to provide more sorted particles. For example, there can be 3, 4, 5 or more outlets for sorting different sized particles.

The pillar array 120 is a deterministic lateral displacement (DLD) array with predefined array parameters. The pillars 125 are periodically arranged with spacing λk, and each downstream row (rows run in the x-axis) is offset laterally from the previous row by the amount δ breaking the symmetry of the array. This array axis forms an angle $\alpha = \tan^{-1}(\delta/\lambda) = \tan^{-1}(\epsilon)$ with respect to the channel walls 150A, 150B and therefore the direction of fluid flow. Because of the array asymmetry, fluid flow in the gaps between the posts/pillars G is partitioned into 1/ε slots. Each of these slots repeats every 1/ε rows so the flow through the array is on average straight. Particles transiting the gap G near a post can be displaced into an adjacent streamline if the particle's radius, or effective radius in the case of tumbling oblong objects such as rods with a defined length, is larger than the slot width in the gap. Therefore, larger particles are deterministically displaced at each post and migrate at an angle α to the flow. Smaller particles simply follow the streamline paths and flow through the array in the direction of fluid flow.

During operation, particles greater than the predefined critical size are displaced laterally (in the x-axis) at each row by a pillar 125 and follow a deterministic path through the array in the so-called "bumping" mode. The trajectory of bumping particles follows the array axis angle α. Particles smaller than the critical size follow the flow streamlines, weaving through the post array in a periodic "zigzag" mode. Therefore, array elements can be tailored to direct specific particle sizes at an angle to the flow by building arrays with design parameters shown in FIG. 1, which include obstacle size/length, spacing between the posts/pillars G, and post/pillar pitch λ. As noted above, asymmetry is determined by the magnitude of the row-to-row shift δ and is characterized by the slope $\varepsilon=\delta/\lambda$, then leading to the final array angle being $\alpha=\tan^{-1}(\varepsilon)$. For a given array angle, the critical particle size for the bumping mode is determined by the ratio between the particle diameter and the pillar spacing and/or gap. However, embodiments have determined that the velocity of the fluid carrying the mixture can be adjusted (tuned) to separate out predefined size/length particles from a mixture, and embodiments are configured to monitor and change the fluid flow velocity in order to sort out the desired size particles. By using these design criteria, streams of beads, cells, and DNA can all been moved deterministically for size-based separation applications, by monitoring and changing the velocity of the fluid through a feedback system.

It should be appreciated that the array elements and any ancillary microfluidic channels and reservoirs can be fabricated in silicon wafers by using standard microfabrication techniques including photolithography and etching. Arrays can also be molded in polydimethylsiloxane (PDMS) by using similarly crafted silicon. For the silicon etch, an optimized deep reactive ion etch (DRIE) can be used to maintain smooth, vertical side walls, ensuring uniform top-to-bottom spacing between posts/pillars. Embodiments are designed to create manufacturable silicon pillar arrays with uniform gaps between the pillars (also referred to as posts) with dimensions in the sub-100 nanometer (nm) regime. These pillar arrays can be used, for example, in a bumper array configuration as described above for the sorting and separation of biological entities at these dimensions, such as DNA, RNA, exosomes, individual proteins, and protein complexes. Particularly, the pillar arrays can be designed with an oxide coating, such as a $SiO_2$ coating which can be used to "heal" variation in the gap size along the entire axis of the pillars.

Figure 2:
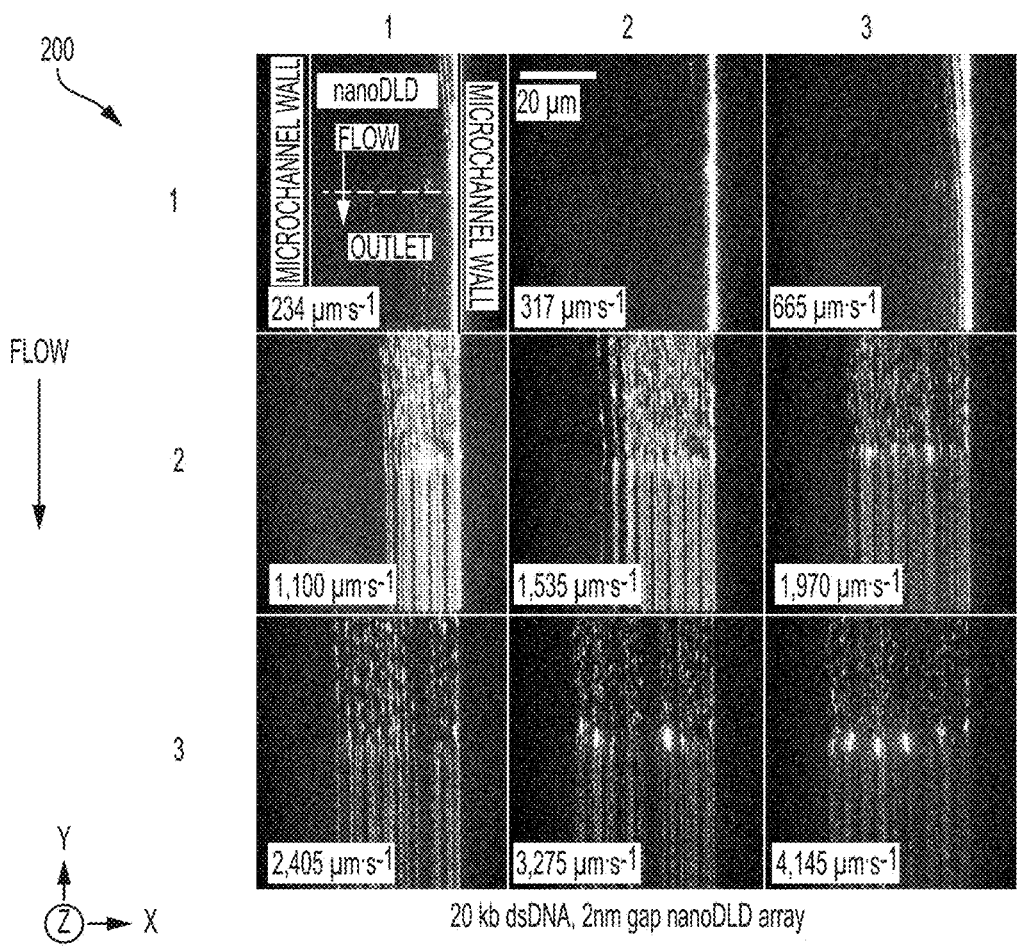
FIG. 2 is a fluorescence microscope composite image showing DNA displacement in a nanoDLD array as a function of velocity according to one or more embodiments.
Figure 3:
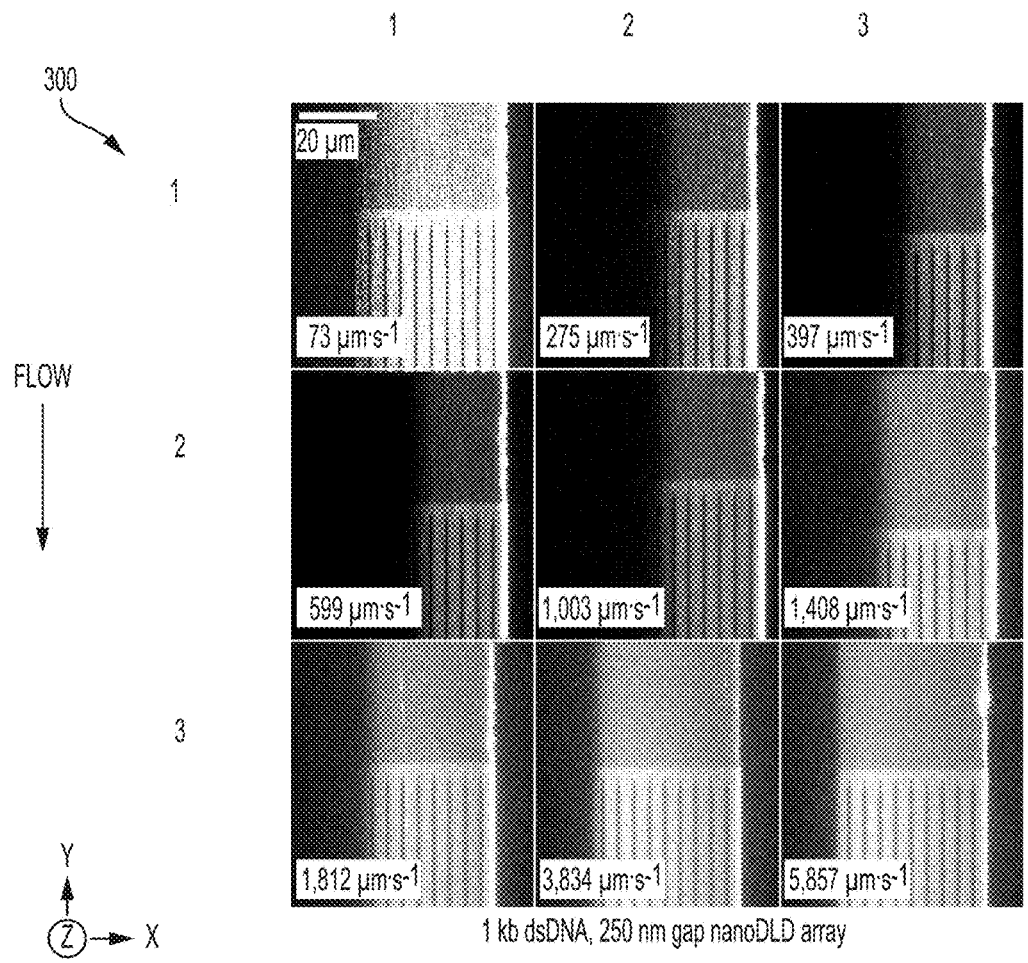
FIG. 3 is a fluorescence microscope composite image showing DNA displacement in a nanoDLD array as a function of velocity according to one or more embodiments.

FIGS. 2 and 3 are fluorescence microscope composite images depicting DNA displacement in a nanoDLD array as a function of velocity, molecular length, and gap size (G) according to one or more embodiments.

Embodiments exploit two main phenomenon of dsDNA in the nanoDLD array 120 as a function of velocity. FIG. 2 depicts for larger strands of double stranded DNA (dsDNA) (e.g., >10 kb), for a given gap size, increasing velocity switches the macromolecule's displacement from bumping to zigzag. Particularly, the fluorescence microscope images 200 are for 20 kb dsDNA in a 250 nm gap nanoDLD array 120. In the grid of fluorescence microscope images 200, row 1 shows 3 fluorescence microscope images with slower velocities ranging from 234 micron per second (μm/s), 317 μm/s, and 665 μm/s, in which the dsDNA (appearing as a white jet/beam) have been laterally displaced to the microchannel wall. It is noted that only the outlet of the nanoDLD array 120 is shown in FIGS. 2 and 3, and in these experiments the inlet (not seen) is being feed with DNA across the entire width. Accordingly, the desired outcome is for the DNA (which are all the same size in FIG. 2) to each be laterally displaced (clumped/sorted) to one side of the nanoDLD array 120 for collection.

FIG. 3 depicts for intermediate strand lengths (e.g., 4-8 kb), for a given gap size, there is a velocity with a maximum displacement angle. Particularly, the fluorescence microscope images 300 are for 1 kb dsDNA in a 250 nm gap nanoDLD array 120. In the grid of fluorescence microscope images 300, the best lateral displacement is seen at speeds between roughly 400-600 $\mu m \cdot s^{-1}$ (sub-images at row 1, column 3 and row 2, column 1). The size of gap G in the nanoDLD shifts the degree of the effect and larger gap sizes (G) show reduced displacement at a given velocity and strand length. Double strand DNA (dsDNA) in a nanoDLD array having a gap size G 25-750 nm exhibits a phenomenon in which slower fluid velocity causes the macromolecule to fully displace (full bump mode) (i.e., to be sorted/deflected laterally in the nanoDLD array). As the velocity increases, the DNA molecule displacement decreases, until there is no effect of the array at higher speeds in FIG. 2. As the size of the DNA molecule decreases, there is a velocity of maximum displacement in FIG. 3, below/above which the displacement decreases. The degree of displacement depends on the macromolecule length (number of basepairs), nanoDLD gap size, and velocity of the fluid.

Embodiments involve deflecting a narrow input jet of DNA molecules using control of the fluid velocity within the nanoDLD array 120. Changing the velocity, or the design of the array, influences the degree to which the DNA jet deflects (i.e., the degree to which the DNA of the desired size laterally moves to the wall). The DNA jet is the input of molecules. As different size DNA molecules deflect to different degrees, this constitutes a particular mechanism for separating DNA as shown in FIG. 4.

Figure 4:
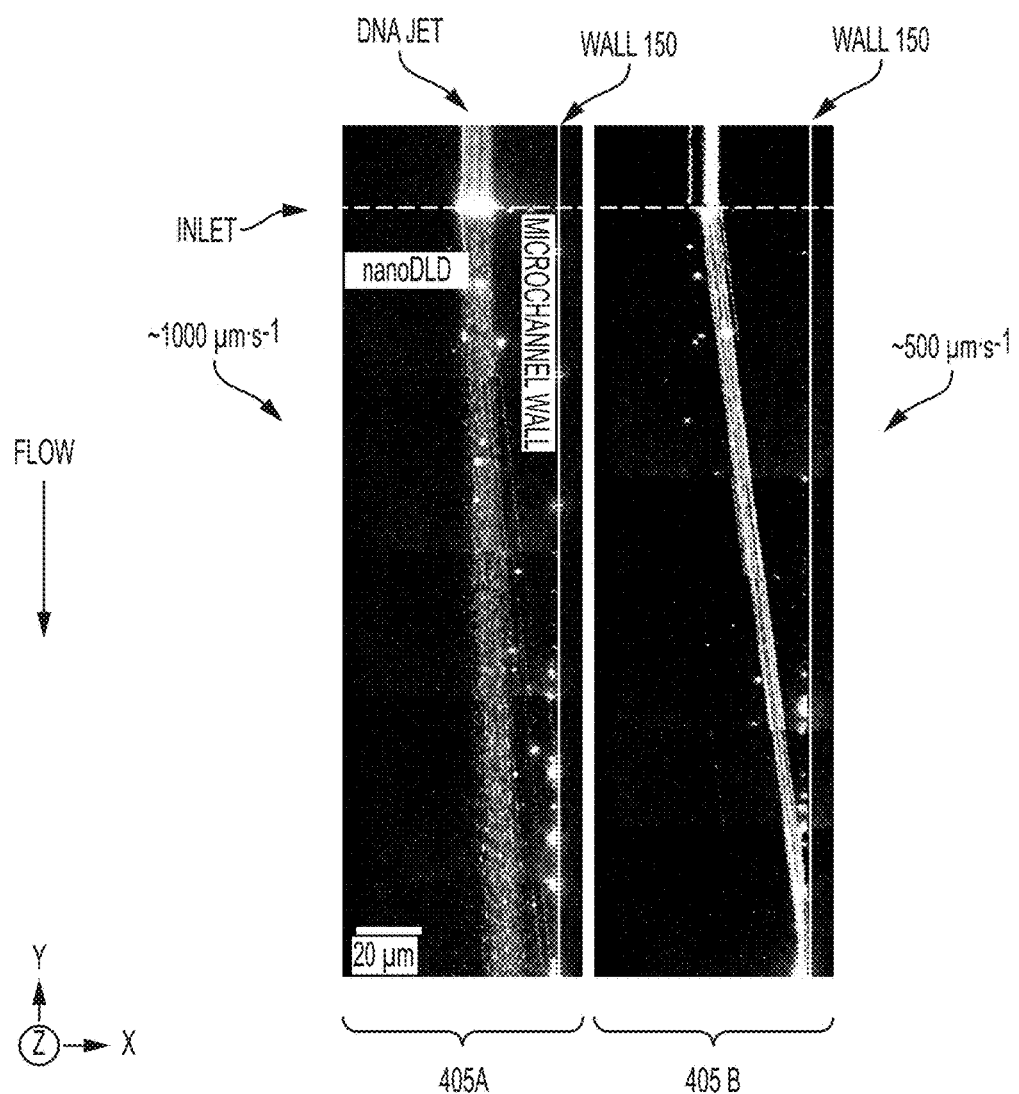
FIG. 4 is a fluorescence microscope composite image showing DNA displacement in the nanoDLD array according to one or more embodiments.
Figure 5:
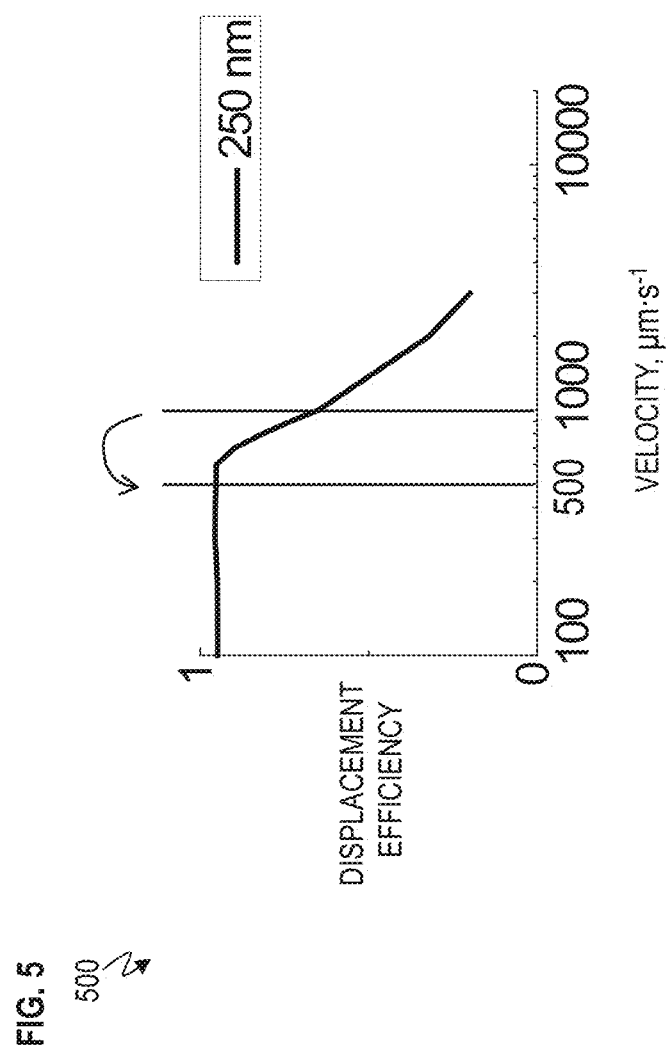
FIG. 5 is a graph of the relationship between the displacement efficiency and velocity plotted for a given gap size and DNA length in FIG. 4 according to one or more embodiments.

FIG. 4 is a fluorescence microscope image depicting DNA displacement in the nanoDLD array 120 according to one or more embodiments. In this example, 10 kb dsDNA is used in a 250 nm gap G nanoDLD array 120 for the fluorescence microscope images 405A and 405B. Control of fluid velocity allows control of dsDNA lateral displacement in the x-axis. The fluorescence microscope image 405A illustrates the flow of 10 kb dsDNA molecules for a velocity of 1000 $\mu m \cdot s^{-1}$. The fluorescence microscope image 405B illustrates the flow of 10 kb dsDNA molecules for a velocity of 500 $\mu m \cdot s^{-1}$. Changing velocity allows tuning of DNA from fully bumping (fully laterally displaced) to fully zigzag (no deflection i.e., no lateral displacement). This allows control of separation resolution. Separation resolution, as would be defined for liquid chromatography, can be as high as 1 or greater at 2σ (where σ is a standard deviation) peak width, implying 95% or better separation. FIG. 5 is a graph 500 of the relationship between the displacement efficiency and velocity plotted for a given gap size (which is a 250 nm gap) and DNA length (number of basepairs, which is 10 kb dsDNA) in FIG. 4 (including fluorescence microscope images 405A and 405B). As can be seen in view 405B and graph 500, the velocity of 500 $\mu m \cdot s^{-1}$ provides the (full/best) lateral displacement of the 10 kb ds DNA molecules to the wall 150 with a thinner jet in contrast to the jet (spread out beam of DNA molecules) in the fluorescence microscope image 405A. Accordingly, the velocity at 500 $\mu m \cdot s^{-1}$ in graph 500 has unity displacement (100%) for the 10 kb ds DNA molecules.

Figure 6:
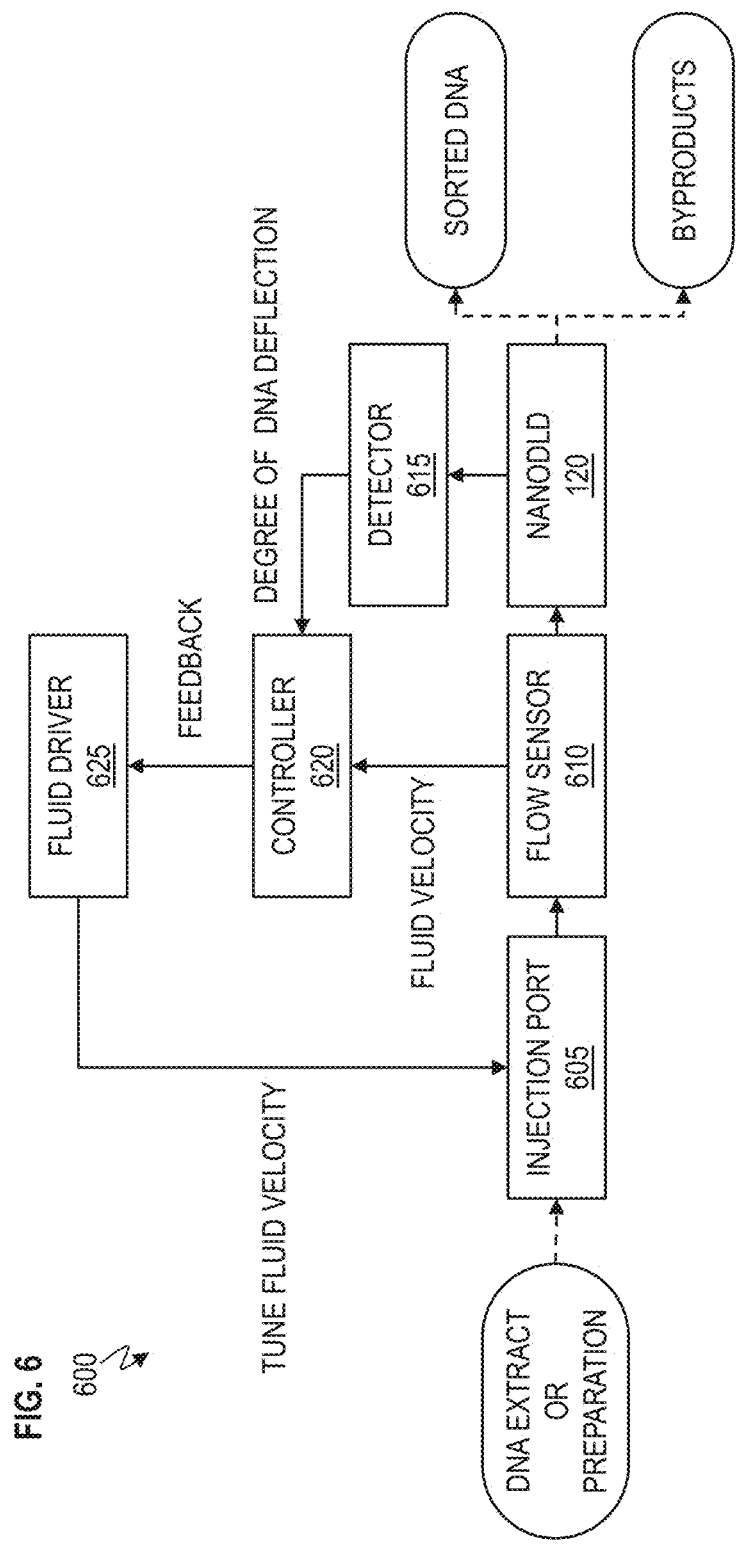
FIG. 6 is a block diagram of a sorting machine for controlling macromolecule (e.g., DNA) separation from a mixture in the nanoDLD array according to one or more embodiments.

FIG. 6 is a block diagram of a machine 600 for controlling molecule (DNA) separation from a mixture in the nanoDLD array 120 according to one or more embodiments. FIG. 10A depicts a machine layout of the machine 600 according to one or more embodiments. FIG. 10B is an enlarged view of the nanoDLD array chip 100 in the machine 600 according to one or more embodiments.

With reference to FIGS. 6, 10A, and 10B, one implementation of the machine 600 for accomplishing DNA separation involves a housing or encasing 1005 which integrates a nanoDLD chip 100 and any fluidic networks and injection ports required for transporting fluid samples into and off of the nanoDLD chip 100, as well as injecting/extracting fluid from the housing 1005. The machine 600 includes a flow sensor 610 that registers the velocity of the fluid in the nanoDLD chip 100. The flow sensor 610 can be embedded in the housing 1005 or mounted separately. In one implementation, the flow sensor 610 can be integrated into the nanoDLD chip 100. Examples of flow sensor 610 can include piezoelectric devices, thermometry, mechanical devices, and electromechanical devices. The fluid velocity is monitored and recorded by a controller 610 which feeds back into a fluid driver 625. Examples of the controller 620 can include a microcontroller, a processor, and/or a computer having a processor, memory, and inputs/outputs. Examples of the fluid driver 625 can include a fluidic pump, a syringe, an electrophoretic setup, or any other mechanism for driving fluids in a controlled manner. The fluid driver 625 can be integrated into the housing 1005 or mounted separately. The fluid driver's output (i.e., velocity of fluid) is configured to be adjusted to match a set point velocity (a desired velocity), and/or execute any pattern of ramping up and down the velocity within the nanoDLD array 120.

A detector 615 can also be incorporated on-chip (e.g., on the nanoDLD chip 100), in the housing 1005, and/or mounted separately, to monitor the DNA jet and separation process. In one implementation, the DNA molecules (and flow) can be detected by the detector 615 through fluorescence microscopy of fluorophore labeled DNA molecules. The detector's output of the detector 615 can be fed into the controller 620 to add another degree of feedback on the fluid velocity, and thus on the separation process. Multiple flow sensors 610 and detectors 615 can be used to increase the accuracy of the separation process. Examples of the detector 615 can include electric transducers, optoelectronic transducers, optical visible/fluorescent microscopy, etc.

Figure 8B:
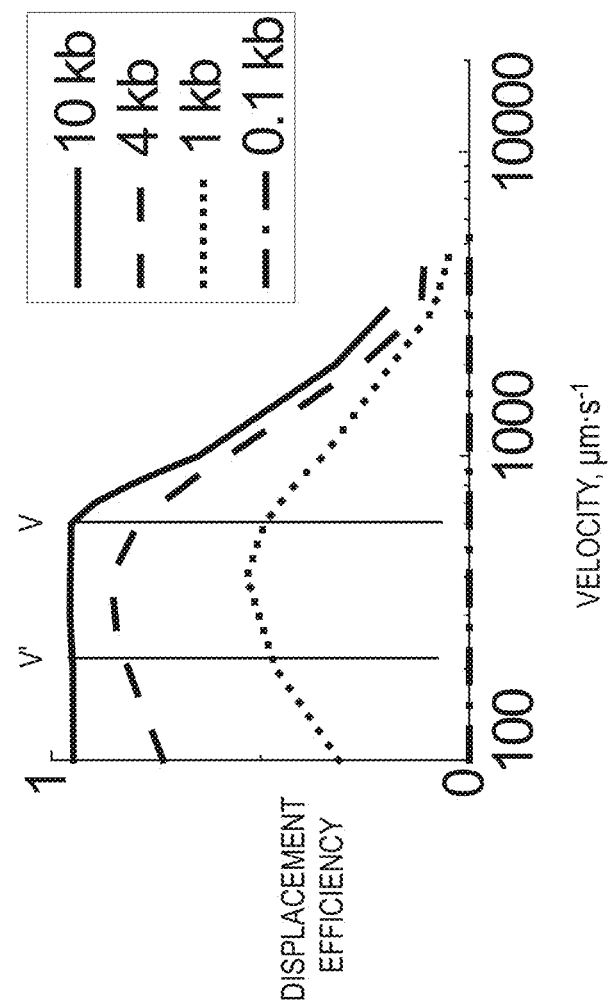
FIG. 8B is a graph depicting the relationship between the displacement efficiency and velocity in FIG. 8A according to one or more embodiments.

In a general operation, a complex mixture of different DNA and RNA strands, reagents, enzymes, macromolecules, molecules, surfactants, salts, catalysts, etc., is fed into the nanoDLD array 120 through an injection port 605 using a fluid driver 625 in the housing 1005. The composition of the mixture can be of any nature, with the one criterion that no particle component is larger than the gap size G of the nanoDLD array 120. The controller 620 is programmed for a set-point velocity at which the desired (target) DNA strand is to separate from the fluid mixture. In the case of separating a DNA molecule from a mixture of smaller molecules, enzymes, catalysts, etc., this requires only displacing the DNA jet (i.e., targeted DNA molecules) from the mixture jet (i.e., byproducts which are everything else that is not the targeted DNA molecules). In the case of separating a (targeted) DNA molecule from several different DNA molecules, two types of modes can be used. In the first type of mode, velocity is controlled such that the target DNA jet deflects (at angle α in bump mode) away from all non-targeted strands (as shown in FIGS. 7A and 7C). Depending on the target DNA length, the speed can be run fast (velocity V in FIGS. 7A and 7C) or slow (velocity V' in FIGS. 7A and 7C) to maximize the deflection difference in the array. In the second type of mode, the velocity is set such that the input mixture jet is split into a spallation of jets (split into multiple jets), each jet containing a different DNA length. This allows multiple DNA strands (of different lengths) to be isolated at once (FIGS. 7A and 8A) and allows for target DNA strand selection in cases where the strand's length is in between larger and smaller non-targeted strands (FIGS. 8A and 8B).

It should be appreciated that the complex mixture (which includes the targeted DNA molecule) is input together (e.g., in the same inlet 105A) into the nanoDLD array 120 of the nanoDLD chip 100. In addition, the mixture is continuously being flowed and separated in the nanoDLD chip 100, allowing continuous operation of the separation process for any required time/volume; no batch or pulse processing scheme is needed.

FIG. 7A is a schematic illustrating that the nanoDLD array 120 is utilized for deterministic lateral displacement according to one or more embodiments. FIG. 7B is an enlarged view illustrating that the nanoDLD array 120 is utilized for deterministic lateral displacement according to one or more embodiments. FIG. 7C is a graph 750 depicting the relationship between the displacement efficiency and velocity plotted for a given gap size and DNA length according to one or more embodiments.

FIG. 7A shows a mixture injection at the inlet in which the larger DNA is deflected (directed) to bump mode to the sorted slot (at angle α) according to a first path, the shorter DNA is deflected (i.e., directed) to another outlet (at a different angle less than angle α) according to a second path, and a third path is the zigzag mode that is practically straight along the fluid flow direction.

The controller 620 is configured to control the velocity of fluid in the nanoDLD array 120 such that the target DNA jet (longer 10 kb DNA) deflects away from all non-targeted strands (shorter 1 kb DNA) as shown in FIGS. 7A and 7C) in this case. In another case, the targeted DNA can be the shorter 1 kb DNA that deflected in less than full bump mode (i.e., less than angle α but greater than zigzag mode) and has been separated from the longer 10 kb DNA that deflected in full bump mode (at angle α). Depending on the target DNA length, the speed can be run fast (velocity V in FIGS. 7A and 7C) or slow (velocity V' in FIGS. 7A and 7C) to maximize the deflection difference in the array. The graph 700 in FIG. 7C shows that the 1 kb DNA and the 10 kb DNA have the greatest lateral distance apart from one another (i.e., the greatest separation) at fluid velocity V' which is approximately 100 µm/s. The greatest lateral distance apart from one another (i.e., the greatest separation) means that the two DNA lengths have a maximum lateral separation from one another in the x-axis of the nanoDLD array 120 in FIG. 7A as controlled (and monitored) by the controller 620. If a higher throughput rate is required, which requires higher fluid velocity, the second greatest lateral distance obtained at velocity V can be used. This would be desirable in cases of increased processing speed or larger volumes.

FIG. 8A is a schematic illustrating that the nanoDLD array 120 utilized for deterministic lateral displacement according to one or more embodiments. FIG. 8B is a graph 800 depicting the relationship between the displacement efficiency (i.e., how far the particles are deflected) and velocity according to one or more embodiments. FIG. 8A illustrates input of a mixture (including fluid) of DNA molecules of different lengths. The controller 620 is configured to control/adjust the velocity of the fluid such that the input mixture jet is split into a spallation of jets (multiple jets), each jet is of a different DNA length. By having the controller 620 monitor and control the fluid velocity through the nanoDLD array 120, this allows multiple strands to be isolated (i.e., laterally displaced from one another according to length) at once into predefined collection slots and allows for target DNA strand selection in cases where the strand's length is in between larger and smaller non-targeted strands. In this example, there are 4 different DNA lengths to be separated which are 0.1 kb dsDNA, 1 kb dsDNA, 4 kb dsDNA, and 10 kb dsDNA. In the graph 850 of FIG. 8B, fluid velocity V' (as controlled by controller 620) has the largest lateral separation/displacement among the 4 DNA lengths (0.1 kb dsDNA, 1 kb dsDNA, 4 kb dsDNA, and 10 kb dsDNA) and fluid velocity V also provides good separation.

Figure 9B:
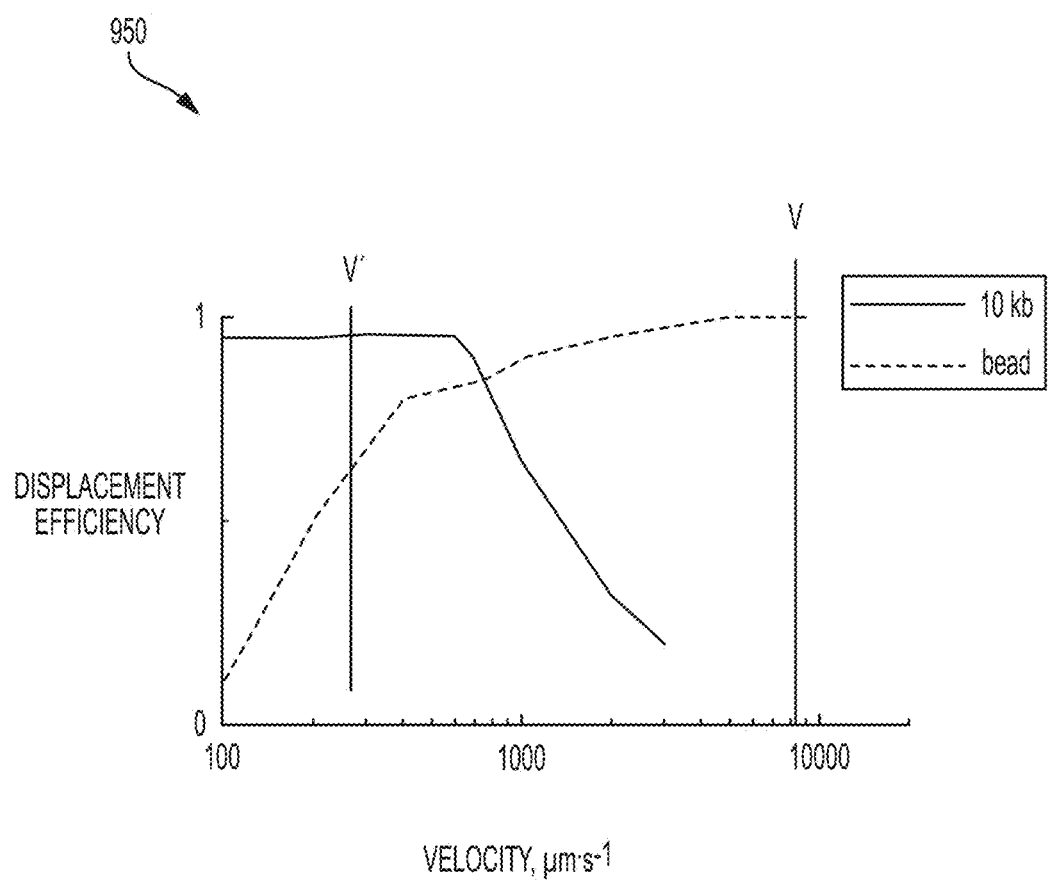
FIG. 9B is a graph depicting the relationship between the displacement efficiency and velocity plotted targeted DNA molecules attached to beads versus non-target DNA molecules in FIG. 9A according to one or more embodiments.

FIG. 9A is a schematic of hybridized bead dsDNA separation according to one or more embodiments. FIG. 9B is a graph 950 depicting the relationship between the displacement efficiency and velocity plotted for a given gap size and for targeted DNA molecules attached to beads (DNA hybridized beads) versus non-target DNA molecules according to one or more embodiments. FIG. 9C depicts an example of hybridizing (i.e., attaching) a single strand DNA bead (ssDNA bead) with its complementary target DNA sequence (target single strand DNA molecules).

There is a non-target single strand DNA molecules which is also referred to as non-target DNA sequences. Also, there is a single strand DNA bead (ssDNA bead), which is a bead attached to a single stand DNA molecule, and the single strand DNA molecule is complementary to the target single strand DNA molecule. The target single strand DNA molecule can be referred to as the target DNA sequence, target DNA strands, etc., because target single strand DNA molecule is targeted to be separated out of the mixture. With all of these particles in a mixture, annealing occurs to hybridize the target DNA sequence to the (complementary) ssDNA bead, thus resulting in the dsDNA bead. The non-targeted DNA sequence does not combine with the ssDNA bead. The combination/hybridization can occur prior to input in the nanoDLD array 120 and/or in the nanoDLD array 120.

FIGS. 9A, 9B, and 9C illustrate that an additional mode can be run using beads to separate target DNA strands from a mixture because the target DNA strands are to form hybridized beads with dsDNA. The dsDNA beads are separated (i.e., lateral displaced) based on velocity, thereby separating the target DNA strands. Inelastic spherical particles, such as plastic beads, have the opposite (i.e., inverse) velocity dependence of DNA. Increasing the velocity (speed) of inelastic spherical particles flowing through the nanoDLD array 120 leads to increasing deflection. At high fluid velocity, DNA strands do not deflect while beads will completely deflect (in bump mode at angle α), with the correct nanoDLD geometry.

In FIGS. 9A, 9B, and 9C, one or more embodiments can involve using beads which have DNA sequences conjugated to their surface (i.e., hybridized beads). The size of the particle and the gap size (G) of the nanoDLD array 120 are chosen such that the particle jet completely deflects at speeds above the DNA zigzag transition. This means that a lower velocity V' (or lower) the DNA molecule (e.g., 10 kb) deflects while the beads have lower a lateral displacement (deflect at less than angle α), thereby allowing the beads to be separated from DNA. However, when the velocity is increased to cross a threshold, the DNA molecules no longer deflect but instead transition into zigzag mode while the beads transition into full bump mode (full deflection), thereby allowing the beads and DNA molecules to be laterally separated from one another in the nanoDLD array 120 at, for example, velocity V.

Accordingly, the DNA on the bead (i.e., DNA attached to bean) is selected as a complimentary sequence to the targeted DNA. Addition of the beads to the initial mixture and annealing hybridizes the target DNA to the beads, thus forming a complex (i.e., dsDNA molecule/complex). The dsDNA bead complex can now be run through the nanoDLD array 120 to remove targeted DNA from all other mixture components. This mode has the advantage of allowing higher throughput with fast flow velocities (such as 10,000 µm/s or faster.

FIGS. 11A and 11B together illustrate flow chart 1100 depicting an example operation the sorting machine 600 according to one or more embodiments. At block 1105, the requisite buffer solution (fluid) is loaded into the fluid driver 625, and the fluid driver 625 is configured to inject the buffer solution into the (nanoDLD device 100), completely wetting the flow sensor 610 and nanoDLD device/chip 100.

At block 1110, a complex mixture that can include different DNA and RNA strands, reagents, enzymes, macromolecules, molecules, surfactants, salts, catalysts, etc., is fed into the nanoDLD array 120 through an injection port in the housing 1005. The composition of the mixture can be of any nature, with the one criterion that no component is larger than the gap size G of the nanoDLD array 120. In one implementation, the complex mixture is fed into the nanoDLD array 120 in a narrow jet on the wall opposite of the sorted slot. The narrow jet can be produced using hydrodynamic focusing through an additional jacket fluid (buffer) injection port, or alternative means such as electrophoretic or electrostatic focusing.

At block 1115, the controller 620 can be programmed with a lateral position set-point for the DNA, which is to be maintained by control of the velocity of the fluid flow via the fluid driver 625. The lateral position of the DNA determines the degree to which the DNA is separated from the complex mixture. The lateral position parameters and the velocity parameter can be selected from calibration experiments, calculation, and/or from in situ tuning of the velocity as described herein. Accordingly, the velocity of the fluid is tuned to maintain and/or create the lateral position set-point for the DNA.

At block 1120, the controller 620 is configured to control the fluid driver 625, to activate the fluid driver 625, to initiate and ramp up the fluid velocity output by the fluid driver 625. The velocity output by the fluid driver 625 is measured by the flow sensor 610.

At block 1125, DNA flows into the nanoDLD array 120. Depending on the fluid velocity, gap size (G), and DNA length, the DNA stream/jet is displaced a certain amount laterally across the array channel of the nanoDLD array 120 as the DNA traverses down the array 120 in the fluid flow direction.

At block 1130, the detector 615 monitors the lateral position of the target DNA. The lateral position information is fed back to the controller 620.

At block 1135, the controller 620 is configured to adjust the velocity of the fluid, via the fluid driver 625, in order to maintain the lateral displacement of the DNA and/or create the desired lateral displacement of the DNA.

There are various techniques for operating the sorting machine 600.

i. In one case, the controller 620 is configured to control/adjust the velocity (of the fluid flowing into and through the nanoDLD array 120) such that the target DNA jet deflects away from all non-targeted strands (FIGS. 7A, 7B, 7C); depending on the target DNA length, the speed can be run fast (velocity V in FIG. 7) or slow (velocity V' in FIG. 7) to maximize the lateral difference/separation between different length DNA molecules flowing in the array 120.

ii. In the case of the complex mixture jet being split into a spallation of jets, for each of the DNA of a different DNA length (FIGS. 8A, 8B), the controller 620 is configured to control/adjust velocity to maximize the number of split jets, and/or the lateral difference between any two deflected jets. In this case, there can be 2, 3, 4, etc., DNA lengths for the DNA molecules, and the controller 620 adjusts the velocity such that the different DNA lengths of molecules are separated into laterally displaced DNA jets as depicted in FIGS. 8A and 8B.

iii. In the case of a DNA and bead mixture (FIGS. 9A, 9B, 9C), the velocity (as controlled by the controller 620) is tuned to a speed high enough that the DNA completely enters a zigzag mode (i.e., does not deflect) with the beads fully deflecting (at angle α). The as described algorithm can be used to tune and determine the optimum velocity, for a given gap and DNA length, for separation of the hybridized dsDNA bead from the mixture. Once the velocity is known for a given DNA separation, the machine 600 can be constructed to exhibit a fixed velocity, e.g., through design of the fluid structure or fixing the controller/fluid driver output.

FIG. 12 is a flow chart 1200 of a method of separating molecules according to one or more embodiments. Reference can be made to FIGS. 1-11 discussed herein. At block 1205, fluid and molecules are provided into a nanoDLD array 120. At block 1210, feedback is received (by controller 620) of a fluid velocity of the fluid flowing through the nanoDLD array 120. At block 1215, the fluid velocity of the fluid is controlled by the controller 620 such that first size molecules (X amount of basepairs or Y bead size) of the molecules are displaced from second size molecules (Z amount of basepairs) of the molecules.

The fluid velocity flowing through the nanoDLD array 120 is controlled by the controller 620 according to a size of the molecules to be separated. In one implementation, the fluid velocity is controlled to be greater than 0 millimeters per second (mm/s) to 1 mm/s in order to separate double stranded DNA molecules of the molecules down to 10 kilo-basepair (kbp) at a first displacement efficiency and down to 1 kbp at a second displacement efficiency. The first displacement efficiency is about or reaches 100% (where 100% displacement efficiency is full bump mode which is full deflection at angle α). The second displacement efficiency is at or reaches 50%, where 50% displacement efficiency is deflection at about half the angle α. The gap size G can range from 10-500 nm. The angle α can range from 1° to 16°, particularly at about 5.7°.

In an implementation, the fluid velocity is controlled to range from about 1 mm/s or greater in order to separate double stranded DNA molecules of the molecules from about 100 to about 500 basepair (bp) at a displacement efficiency. The displacement efficiency is about 20% or greater, which is a deflection of about 20% of the angle α. In another case, the displacement frequency is about 5% or greater. The gap size G can range from 10-100 nm. The angle α can range from 1° to 16°, particularly at about 5.7°.

The fluid velocity is controlled to range from about 50 μm/s to about 5000 μm/s in order to separate DNA molecules of the molecules ranging from about 1 kbp to about 50 kbp at a displacement efficiency of 20% or greater. The gap size G can range from 50-250 nm. The angle α can range from 1° to 16°, particularly at about 5.7°.

One or more embodiments include a system for separation of a mixture. The system includes a nano-deterministic lateral displacement (nanoDLD) array 120 configured to separate the mixture in a fluid, and a feedback system configured to control a velocity of the fluid through the nanoDLD array 120. The feedback system is configured to control the velocity of the fluid to separate one or more entities. The feedback system is configured to control the velocity to cause a first type of the one or more entities be laterally displaced in a first direction and to cause a second type of the one or more entities to be laterally displaced in a second direction. The first type and the second type of the one or more entities are different sizes (e.g., different lengths). The feedback system includes a controller 620. The controller 620 is configured to adjust the velocity of the fluid flowing through the nanoDLD array 120 in order to separate the one or more entities. The feedback system includes a detector 615, in which the detector 615 is configured to monitor the velocity of the fluid flowing through the nanoDLD array 120. A fluid driver 625 is configured to inject the fluid into the nanoDLD array 120, where the fluid driver 625 is configured to be controlled by the controller 620. A flow sensor 610 is configured to monitor the velocity of the fluid being injected into the nanoDLD array 120. The controller 620 is configured to receive input from the flow sensor 610 and the detector 615, in which the controller 620 is configured to change the velocity based on the input received from the flow sensor 610 and the detector 615.

FIG. 13 is a flow chart 1300 of method of separating targeted sequence molecules from a mixture according to one or more embodiments. Reference can be made to FIGS. 1-12. At block 1305, a mixture is provided/loaded into a nanoDLD array 120. The mixture includes non-targeted molecules, the targeted sequence molecules (e.g., DNA strands of a particular sequence), and a complimentary strand (of the targeted DNA stands) attached to colloidal particles. Hybridized colloidal particles are formed by hybridization of the targeted sequence molecules and the complimentary strand attached to the colloidal particles.

At block 1310, the hybridized colloidal particles are separated from the non-targeted molecules based on the hybridized colloidal particles following a lateral displacement behavior of spherical colloids, as depicted in FIGS. 9A, 9B, 9C. The hybridized colloidal particles following the lateral displacement behavior of the spherical colloids is different from a lateral displacement behavior of the non-targeted molecules in the nanoDLD array 120.

A velocity of the mixture is controlled to about 0.5 mm/s and greater to thereby separate out the hybridized colloidal particles from the non-targeted molecules. The hybridized colloidal particles can be formed in the nanoDLD array 120, prior to being input into the nanoDLD array 120, and/or both in the nanoDLD array 120 and prior to being input into the nanoDLD array 120.

Technical effects and benefits include a method and structure for separation of DNA molecules using nanoDLD pillar arrays. Technical benefits further provide allow continuous, spatial separation of double stranded deoxyribonucleic acid (dsDNA) based on the length of the DNA (a.k.a. the number of basepair molecules within the DNA strand), at a single strand resolution, and within a length range of 10,000 basepairs or more, down to 100 basepairs. Embodiments can be used with small sample sizes such as, e.g., 2-10 $\mu L^{-1}$, in low concentrations such as 1 picogram·$\mu L^{-1}$ or higher.

Deposition is any process that grows, coats, or otherwise transfers a material onto the wafer. Available technologies include, but are not limited to, thermal oxidation, physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer. Examples of removal include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist, and then a machine called a stepper focuses, aligns, and moves a mask, exposing select portions of the wafer below to short wavelength light. The exposed regions are then washed away by a developer solution. After etching or other processing, the remaining photoresist is removed. Patterning also includes electron-beam lithography, nanoimprint lithography, and reactive ion etching.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The term "about" and variations thereof are intended to include the degree of error associated with measurement of the particular quantity based upon the equipment available at the time of filing the application. For example, "about" can include a range of ±8% or 5%, or 2% of a given value.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described herein. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A system for separation of nucleic acids, the system comprising:
   a nano-deterministic lateral displacement (nanoDLD) array configured to separate the nucleic acids in a fluid, wherein the nanoDLD array comprises
   (a) a critical angle alpha of about 5 degrees to about 6 degrees and
   (b) a gap between pillars of about 50 nanometers to about 250 nanometers; and
   a feedback system configured to control a velocity of the fluid through the nanoDLD array, wherein the feedback system is configured to control the velocity of the fluid to greater than 0 micrometers per second to about 600 micrometers per second to separate one or more nucleic acids.

2. The system of claim 1, wherein the feedback system is configured to control the velocity to cause a first type of the one or more nucleic acids laterally displaced in a first direction and to cause a second type of the one or more nucleic acids to be laterally displaced in a second direction.

3. The system of claim 2, wherein the first type and the second type of the one or more nucleic acids are different sizes.

4. The system of claim 1, wherein the feedback system includes a controller.

5. The system of claim 4, wherein the controller is configured to adjust the velocity of the fluid flowing through the nanoDLD array in order to separate the one or more nucleic acids.

6. The system of claim 5, wherein the feedback system includes a detector, the detector configured to monitor the velocity of the fluid flowing through the nanoDLD array.

7. The system of claim 6, wherein a fluid driver is configured to inject the fluid into the nanoDLD array, the fluid driver configured to be controlled by the controller.

8. The system of claim 7, wherein a flow sensor is configured to monitor the velocity of the fluid being injected into the nanoDLD array.

9. The system of claim 8, wherein the controller is configured to receive input from the flow sensor and the detector, the controller being configured to change the velocity based on the input received from the flow sensor and the detector.

10. A method of separating nucleic acids, the method comprising:
    providing fluid and nucleic acids into a nano-deterministic lateral displacement (nanoDLD) array, wherein the nanoDLD array comprises
    (a) a critical angle alpha of about 5 degrees to about 6 degrees and
    (b) a gap between pillars of about 50 nanometers to about 250 nanometers;
    receiving feedback of a fluid velocity of the fluid flowing through the nanoDLD array; and
    controlling the fluid velocity of the fluid such that a first size nucleic acids are displaced from second size nucleic acids, wherein the fluid velocity is controlled to be greater than 0 micrometers per second to about 600 micrometers per second.

11. The method of claim 10, wherein the fluid velocity is controlled to separate double stranded DNA, wherein a first displacement efficiency of a double stranded DNA of 10 kb or more is about 100%, and wherein a second displacement efficiency of a double stranded DNA of 1 kb to less than 10 kb is about 50%.

12. The method of claim 10, wherein the fluid velocity is controlled to separate double stranded DNA from about 100 to about 500 basepair (bp) at a displacement efficiency of 5% or greater.

13. The method of claim 12, wherein the displacement efficiency is about 20% or greater.

14. The method of claim 10, wherein the fluid velocity is controlled to separate DNA molecules from about 1 kbp to about 50 kbp at a displacement efficiency of 20% or greater.

15. A method of separating targeted nucleic acids, the method comprising:
providing a mixture into a nano-deterministic lateral displacement (nanoDLD) array, wherein the mixture includes nontargeted nucleic acids, the targeted nucleic acids, and a complimentary strand attached to colloidal particles, and wherein hybridized colloidal particles are formed by hybridization of the targeted nucleic acids and the complimentary strand attached to the colloidal particles; and
separating the hybridized colloidal particles from the non-targeted nucleic acids based on the hybridized colloidal particles following a lateral displacement behavior of spherical colloids,
wherein a fluid velocity is controlled to be greater than 100 micrometers per second to about 600 micrometers per second.

16. The method of claim 15, wherein the hybridized colloidal particles following the lateral displacement behavior of the spherical colloids is different from a lateral displacement behavior of the non-targeted nucleic acids.

17. The method of claim 16, wherein a velocity of the mixture is controlled to about 500 micrometers per second to about 600 micrometers per second to thereby separate out the hybridized colloidal particles from the non-targeted nucleic acids.

18. The method of claim 15, wherein the hybridized colloidal particles are formed in the nanoDLD array, prior to being input into the nanoDLD array, or both in the nanoDLD array and prior to being input into the nanoDLD array.

* * * * *